US00PP26025P2

(12) United States Plant Patent
Marek

(10) Patent No.: US PP26,025 P2
(45) Date of Patent: Oct. 27, 2015

(54) ***NANDINA* PLANT NAMED 'TWILIGHT'**

(50) Latin Name: *Nandina domestica*
Varietal Denomination: TWILIGHT

(71) Applicant: Neil Marek, Magnolia, TX (US)

(72) Inventor: Neil Marek, Magnolia, TX (US)

( * ) Notice: Subject to any disclaimer, the term of this patent is extended or adjusted under 35 U.S.C. 154(b) by 31 days.

(21) Appl. No.: 14/120,142

(22) Filed: Apr. 28, 2014

(51) Int. Cl.
*A01H 5/00* (2006.01)

(52) U.S. Cl.
USPC ..... Plt./235

(58) Field of Classification Search
USPC ..... Plt./235
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Nandina* cultivar named 'TWILIGHT' is disclosed, characterized by distinctive pink, white and green foliage, which changes color with maturity. Plants have unique pink colored stems and petioles on new growth. The new cultivar is a *Nandina*, suitable for ornamental garden purposes.

3 Drawing Sheets

Latin name of the genus and species: *Nandina domestica.* Variety denomination: 'TWILIGHT'.

BACKGROUND OF THE INVENTION

The new cultivar is a product of chance discovery by the inventor. This new variety, hereinafter referred to as 'TWILIGHT', was discovered as a naturally occurring, whole plant mutation by the inventor, Neil Marek. The interesting new mutation was discovered in a commercial laboratory in Magnolia, Tex. among a population of *Nandina domestica* 'Gulf Stream', U.S. Plant Pat. No. 5,656 during May of 2010.

After identifying the new variety as a potentially interesting selection, the inventor first organized propagation of 'TWILIGHT' by tissue culture at the same commercial laboratory during May of 2010. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'TWILIGHT' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TWILIGHT' These characteristics in combination distinguish 'TWILIGHT' as a new and distinct *Nandina* cultivar:

1. Unique color change of foliage: Youngest new foliage is pink, with white variegation. Older immature foliage is bright green with pink and white variation. Mature foliage is green with white variegation, eventually changing to solid green.
2. Pink petiole and stem coloration of new growth.

COMPARISON TO PARENT VARIETY

'TWILIGHT' is similar in most horticultural characteristics to the parent variety *Nandina domestica* 'Gulf Stream', including plant habit. Plants of the new cultivar 'TWILIGHT' however, produce unique variegated foliage, which changes color during the seasons, whereas the parent variety has foliage without variegation. Additionally, stem color of the new growth is different in the new variety.

COMMERCIAL COMPARISON

'TWILIGHT' can be compared to the commercial variety *Nandina domestica* 'Seika' U.S. Plant Pat. No. 21,891. Plants of the new cultivar 'TWILIGHT' are similar to plants of 'Seika' in most horticultural characteristics. Plants of the new cultivar 'TWILIGHT' however, produce unique variegated foliage, which changes color during the seasons, whereas 'Seika' has foliage without variegation. Additionally, stem color of the new growth is different in the new variety.

BRIEF DESCRIPTION OF THE PHOTOGRAPHS

The accompanying photograph in FIG. 1 illustrates in full color a typical plant of 'TWILIGHT' grown outdoors in Magnolia, Tex. The plant is approximately 1.5 years old, and is shown in a three gallon container.

Figure 1:
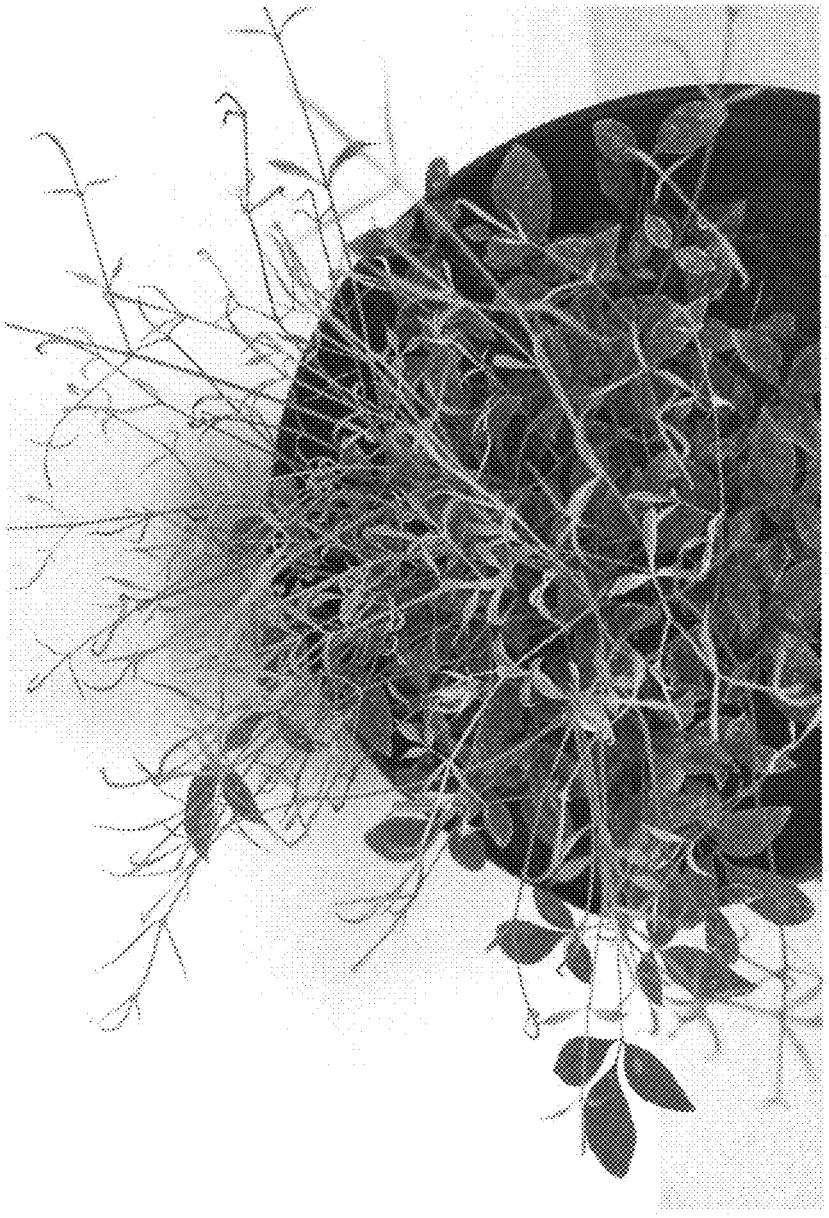
Figure 2:
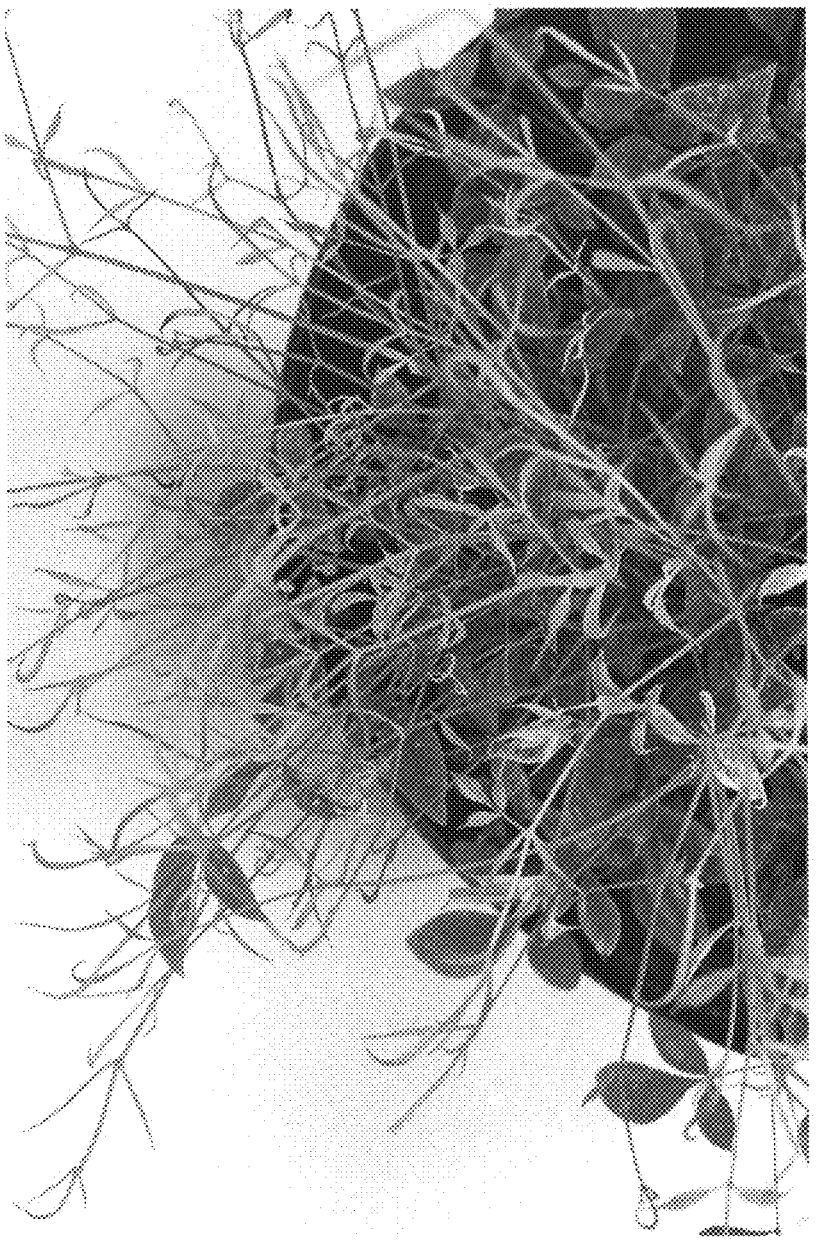
FIG. 2 shows a close up of typical foliage of the new variety.
Figure 3:
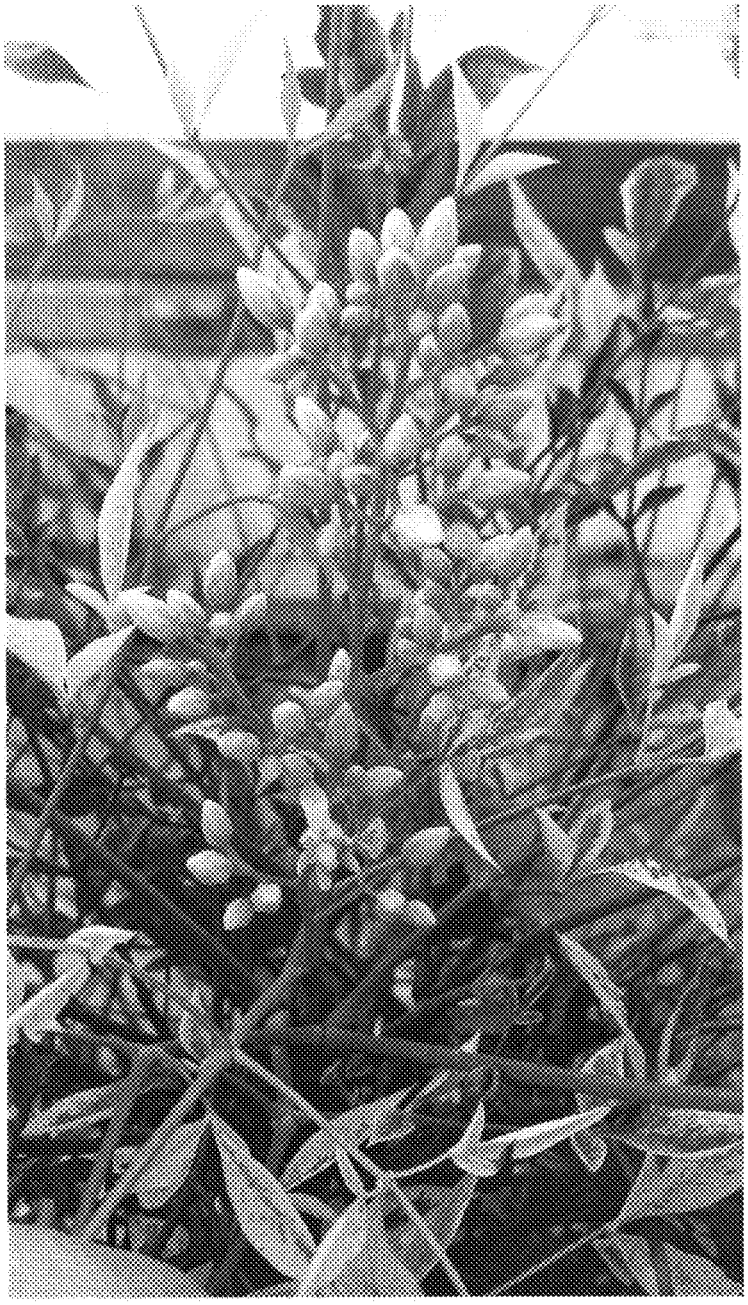
FIG. 3 illustrates flowering panicles.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'TWILIGHT' plants grown outdoors in Magnolia. Tex. Plants are approximately 1.5 years old, in a 3 gallon nursery container. Measurements and numerical values represent averages of typical plant types.

Botanical classification: *Nandina domestica* 'TWILIGHT'.

PROPAGATION

Typically by tissue culture.

Root description: Fine, fibrous young roots, very well branched. Colored near RHS Grey-Brown 199A.

PLANT

Growth habit: Compact shrub. Fine, airy and delicate appearance, outwardly spreading, as an inverted "V" shape.

Height: Approximately 18 cm to top of foliar plane.

Plant spread: Approximately 18 cm.

Branching characteristics: The plant, when produced from a tissue culture plantlet, begins as a clump of stems. Approximately 10 to 15 closely growing clumps per plant, with approximately 5 to 15 leaves per clump. Foliage grows directly from these basal stems.

Stems:

*Length.*—Average 3 to 6 cm.

*Diameter.*—Average 0.4 cm.

*Strength.*—Very strong, difficult to break.

*Color.*—Prominent upper growth colored near Red-Purple 59A. Lower stem near Yellow-Green N144D.

*Texture.*—Glabrous.

Lateral branches: Lateral branches not observed.

Age of plant described: Approximately 1.5 years.

FOLIAGE

Leaf: Alternate, tripinnately compound, with an overall deltoid shape. Average leaf 14 cm long and 12 cm wide.

Leaflets:

*Shape.*—Ovate.

*Quantity and arrangement.*—Approximately 11 per leaf. Terminal leaflet arrangement in 3, lower leaflets occur in opposite pairs. All leaflets sessile.

*Average length.*—2.7 cm.

*Average width.*—1.7 cm.

Individual leaf blades:

*Shape of blade.*—Broad elliptic.

*Apex.*—Acute.

*Base.*—Attenuate.

*Margin.*—Entire.

*Texture of top surface.*—Glabrous.

*Texture of bottom surface.*—Glabrous.

*Appearance of top surface.*—Matte.

*Appearance of bottom surface.*—Matte.

*Aspect.*—Flat to very minutely reflexed downward.

*Color.*—Youngest foliage upper side: Near RHS Red 49B and Red 49C. Mottled with White 155A. Youngest foliage under side: Near RHS Red 49B and Red 49C. Intermediate foliage upper side: Green; near RHS 137C, heavily mottled, White 155A. Apex entirely White 155A. Intermediate foliage under side: Green; near RHS 137D, heavily mottled, White 155A. Mature foliage upper side: Green; near RHS 137B. Infrequently mottled along margin near Yellow-Green 145B. Mature foliage under side: Near RHS Green 138B.

*Venation.*—Type: Pinnate. Venation color upper side: Indistinguishable from leaf blade, at all levels of maturity. Venation color under side: Indistinguishable from leaf blade, at all levels of maturity.

*Petiole.*—Length: Average 5 cm. Diameter: 0.2 cm. Color: Youngest: Near RHS RHS Red 49C. Intermediate: Near RHS Green 137C. Mature: Near RHS Yellow-Green N144A. Texture: Glabrous, moderately glossy.

*Stipule description.*—No stipules present.

FLOWER

Flowering does not occur consistently. Typically, if plants do set flower buds, flowers begin to open early May.

Inflorescence:

*Arrangement.*—Panicle.

*Height.*—Approximately 7 cm.

*Width.*—Approximately 3 cm.

*Quantity of flowers per inflorescence.*—Approximately 60.

Bud:

*Bud shape.*—Ovoid.

*Bud length.*—Approximately 0.7 cm.

*Bud diameter.*—Approximately 0.3 m.

*Bud color.*—Near RHS White N155B, flushed Red 55B, proximal end.

Individual flower:

*Type of individual flowers.*—Single, rotate flower, petals not overlapping.

*Diameter of entire flower.*—Approximately 0.5 cm.

*Length of flower.*—Approximately 1.0 cm.

*Persistent or self-cleaning.*—Self-cleaning.

Petals:

*Length of petal.*—Approximately 3.5 mm.

*Width of petal.*—Approximately 2 mm.

*Apex.*—Acute.

*Base.*—Blunt.

*Shape of petal.*—Oval.

*Petal margin.*—Entire.

*Petal arrangement.*—Even, non-overlapping whorl.

*Petal number.*—6 petals.

*Petal appearance.*—Matte.

*Petal texture.*—Smooth, glabrous.

Color:

*Upper surface.*—Near RHS Yellow 13A.

*Under surface.*—Near RHS White N155D.

OTHER CHARACTERISTICS

Disease and pest resistance: Not observed to be susceptible nor resistant to normal diseases and pests of *Nandina domestica.*

Temperature tolerance: USDA Zone 6 through 11.

Fruit/seed production: Not observed to date.

What is claimed is:

1. A new and distinct cultivar of *Nandina* plant named 'TWILIGHT' as herein illustrated and described.

* * * * *